United States Patent
Venturini et al.

(10) Patent No.: US 11,801,059 B2
(45) Date of Patent: Oct. 31, 2023

(54) SYSTEM AND METHOD FOR DRIVING AN ULTRASONIC DEVICE

(71) Applicant: Orthofix S.R.L., Bussolengo (IT)

(72) Inventors: Daniele Venturini, Povegliano Veronese (IT); Mario Donnici, Bussolengo (IT); Pieralbino Colombo, Treviglio (IT); Alessandro Finezzo, Verona (IT); Gianluca Zandona', Verona (IT)

(73) Assignee: Orthofix S.R.L., Bussolengo (IT)

( * ) Notice: Subject to any disclaimer, the term of this patent is extended or adjusted under 35 U.S.C. 154(b) by 877 days.

(21) Appl. No.: 16/717,841

(22) Filed: Dec. 17, 2019

(65) Prior Publication Data
US 2020/0268393 A1    Aug. 27, 2020

(30) Foreign Application Priority Data

Feb. 21, 2019 (EP) .................................. 19158490

(51) Int. Cl.
*A61B 17/16* (2006.01)
*A61B 17/32* (2006.01)
(Continued)

(52) U.S. Cl.
CPC .. *A61B 17/1626* (2013.01); *A61B 17/320068* (2013.01); *A61B 17/8847* (2013.01);
(Continued)

(58) Field of Classification Search
CPC .............. A61B 17/072; A61B 17/1659; A61B 17/2202; A61B 17/8847; A61B 17/320068; A61B 18/149; A61B 18/1492; A61B 90/98; A61B 2017/0003; A61B 2017/00106; A61B 2017/00123;
(Continued)

(56) References Cited

U.S. PATENT DOCUMENTS

| 4,965,532 A | * | 10/1990 | Sakurai | B06B 1/0253 331/65 |
| 5,001,649 A | * | 3/1991 | Lo | B06B 1/0253 331/181 |

(Continued)

FOREIGN PATENT DOCUMENTS

| EP | 1199042 A2 | 4/2002 |
| GB | 2288120 A | 10/1995 |

OTHER PUBLICATIONS

European Patent Office, "European Search Report," for EP Application No. 18158490.3, dated Jul. 30, 2019.
(Continued)

*Primary Examiner* — Scott A Smith
(74) *Attorney, Agent, or Firm* — HAYNES AND BOONE, LLP

(57) ABSTRACT

A system for driving an ultrasonic device for bone cement removal and/or osteotomy operations comprises a control unit, a memory unit, and a connector for connecting together the control unit and a handset of the ultrasonic device. The control unit is configured to send a signal to the handset, receive from the handset a response to the signal sent, and check an operating condition of the ultrasonic device based on this response. Related device, method and computer program are also disclosed.

21 Claims, 4 Drawing Sheets

(51) Int. Cl.
*A61B 17/88* (2006.01)
*A61B 18/14* (2006.01)
*A61B 17/00* (2006.01)
*A61B 90/98* (2016.01)

(52) U.S. Cl.
CPC ........ *A61B 18/1492* (2013.01); *A61B 18/149* (2013.01); *A61B 90/98* (2016.02); *A61B 2017/0003* (2013.01); *A61B 2017/00084* (2013.01); *A61B 2017/00119* (2013.01); *A61B 2017/00402* (2013.01)

(58) Field of Classification Search
CPC ....... A61B 2017/00137; A61B 17/1626; A61F 2/4607; A61F 2/4671
USPC .......... 227/19, 175.1, 180.1; 606/1, 39, 169, 606/219, 79
See application file for complete search history.

(56) References Cited

U.S. PATENT DOCUMENTS

| | | | | |
|---|---|---|---|---|
| 5,400,267 A | * | 3/1995 | Denen | H02J 3/00 323/911 |
| 6,066,135 A | * | 5/2000 | Honda | B06B 1/0223 607/101 |
| 6,511,478 B1 | * | 1/2003 | Burnside | A61B 18/1492 606/41 |
| 6,756,909 B2 | * | 6/2004 | Wiener | A61B 90/98 702/65 |
| 2002/0049552 A1 | * | 4/2002 | Wiener | A61B 17/320068 702/72 |
| 2005/0020967 A1 | * | 1/2005 | Ono | A61B 17/2202 606/169 |
| 2005/0119666 A1 | | 6/2005 | Bubb | |
| 2008/0125786 A1 | * | 5/2008 | Bubb | A61F 2/4607 606/99 |
| 2010/0125292 A1 | * | 5/2010 | Wiener | A61B 17/320068 606/169 |
| 2015/0088154 A1 | * | 3/2015 | Vaitekunas | B06B 1/0269 606/128 |
| 2016/0175000 A1 | * | 6/2016 | Akagane | A61B 18/149 606/169 |
| 2016/0325121 A1 | | 11/2016 | Kawashima et al. | |

OTHER PUBLICATIONS

International Search Authority, International Search Report and Written Opinion, for PCT/EP2020/054220, dated Apr. 24, 2020, 14 pages.

* cited by examiner

SYSTEM AND METHOD FOR DRIVING AN ULTRASONIC DEVICE

BACKGROUND

Field of application

The present disclosure relates to a system and to a corresponding method for driving an ultrasonic device, used for example to remove bone cement or to perform osteotomy operations, and the following description is made with reference to this application field with the only purpose of simplifying the exposition thereof.

The present disclosure relates to a system and to a corresponding method for driving an ultrasonic device, used for example to remove bone cement or to perform osteotomy operations, and the following description is made with reference to this application field with the only purpose of simplifying the exposition thereof.

Description of the Related Art

As is well-known in this technical field, during prosthesis revision procedures there is often the need to remove bone cement made of polymethyl methacrylate (PMMA). This is a very delicate procedure and an incorrect execution thereof risks causing serious damage to the bone tissue.

There are ultrasonic devices which are able to remove the bone cement by means of special tools to which ultrasounds are transmitted. This simplifies the removal of the bone cement during prosthesis revision procedures since the action of the ultrasounds causes softening of the cement which keeps the implant in position. The tools are therefore positioned so as to collect and remove the softened cement from the host bone. This technique reduces the manual effort and allows the risk of bone fractures and perforations to be reduced.

Ultrasonic devices are also used in osteotomy operations for cutting bone portions, where a blade is moved in a predefined manner by means of ultrasounds.

The known ultrasonic systems generally envisage the presence of a generator to which a handset containing the ultrasound generating elements is connected, said generator allowing powering of the handset and setting its operating parameters. The tools to which the ultrasounds are transmitted during the operations are then connected to the handset, these tools contacting the bone cement or the bone.

According to some known solutions, the generator comprises two separate connection elements for two separate handsets, more specifically a connection element for a first handset intended to remove the bone cement, and a different connection element for a further handset intended for osteotomy operations.

Furthermore, according to some known solutions, the generator is able to store a plurality of operating parameters relating to different types of operation modes, and to use these parameters once the particular desired operation mode—for example the particular operation to be performed—has been selected by the operator.

However, the solutions available hitherto have a number of drawbacks, including the lack of effective feedback for the operator as regards the condition of the handset and/or the tools connected thereto, as well as the absence of a system for helping the operator to correctly set the operating parameters.

There is therefore the need to provide a system which ensures improved interaction with the operator. In particular, it is desirable to provide a driving system for an ultrasonic device having structural and functional features so as to allow overcoming the limitations and drawbacks which still affect the known solutions, in particular able to allow an improved interaction with the operator, while simplifying the use of the ultrasonic device and limiting the possibility of errors during setting-up thereof.

SUMMARY OF THE DISCLOSURE

The present disclosure provides an ultrasonic device with a driving/control system configured to send to a handset of the device an input signal and to measure the characteristic response of the handset and/or the tool associated with the handset to this input signal, this response being compared with expected responses previously stored in the memory of the driving system. In this way, the present disclosure allows data exchange between the handset and the driving system, providing the operator with useful information such as feedback about the state of the handset and the type of tools associated with it and/or their state.

More in particular, an exemplary system for driving an ultrasonic device for bone cement removal and/or osteotomy operations comprises a control unit, a memory unit, and connection means for connecting together the control unit and a handset of the ultrasonic device, the control unit being configured to send a signal to the handset, receive from the handset a response to the signal sent, and check an operating condition of the ultrasonic device based on this response.

According to one aspect of the present disclosure, the operating condition of the ultrasonic device checked by the control unit may comprise at least one of the state of a piezoelectric transducer of the handset, the type of tool associated with the handset, and/or the state of this tool.

In the context of the present disclosure, the term "type of tool" is used to identify both single tools and a class of tools having common features (for example a common shape and/or function).

According to one aspect of the present disclosure, the signal sent may be a signal with a frequency variable within a predetermined frequency range, and, based on the response, the control unit may be configured to calculate at least one parameter indicative of the frequency response of the ultrasonic device.

In particular, this parameter may be the variation in impedance as a function of frequency, thus providing an impedance curve representing the frequency response of the ultrasonic device.

According to one aspect of the present disclosure, the control unit may be configured to compare the response received with data stored in the memory unit, said memory unit comprising data relating to the expected frequency response for the tool associated with the handset and/or data relating to the expected frequency response for the piezoelectric transducer of the handset.

According to one aspect of the present disclosure, the control unit may be configured to measure the characteristic impedance of the piezoelectric transducer of the handset upon variation of the frequency of the signal sent when the tool is not associated with the handset, said control unit being further configured to display the frequency response curve of the piezoelectric transducer and/or compare it with expected values.

According to one aspect of the present disclosure, the control unit may be configured to measure the characteristic impedance of the tool upon variation of the frequency of the signal sent and compare this characteristic impedance with values stored in the memory unit and expected for said tool, said control unit being configured to compare at least the measured resonance frequency with the expected frequency.

In other words, the control unit may be configured to measure the impedance of the tool associated with the handset or, in the case the tool is not associated with the handset, the impedance of the piezoelectric transducer of the handset upon variation of the frequency of the signal sent, and the memory unit comprises data relating to the frequency response expected for the tool associated with the handset and data relating to the frequency response expected for the piezoelectric transducer of the handset, the control unit being further configured to display said frequency response curve of the piezoelectric transducer and/or to compare it with expected values stored in said memory unit. The control unit may then be configured to compare at least the measured resonance frequency with a stored expected frequency.

More particularly, the control unit may be configured to compare different mathematical characteristics of the measured impedance curve, including maximum values, minimum values, first derivative and second derivative, with the characteristics of known impedance curves which have been previously stored; in this way, a comparison between the resonance frequencies is indirectly performed.

According to another aspect of the present disclosure, the control unit may be configured to select from the memory unit an operation mode from a plurality of stored operation modes, as well as to generate an error in the event that the response received from the handset does not correspond to stored data associated with the selected operation mode, wherein said stored data comprises at least the characteristic frequencies of the ultrasonic device.

According to another aspect of the present disclosure, the control unit may be adapted to implement an automatic learning procedure which adopts machine learning and/or artificial intelligence techniques.

According to another aspect of the present disclosure, the system may comprise a user interface configured to allow the entering and/or displaying of operating parameters and/or the selection of an operation mode from a plurality of operation modes whose operating parameters have been stored beforehand in the memory unit.

Furthermore, the control unit may be configured to communicate with and to receive data from an electronic unit incorporated in the handset. In particular, such data may comprise at least the serial number of the handset.

According to another aspect of the present disclosure, the control unit may comprise a control board and a computerized unit which includes the memory unit, in data communication with each other.

According to yet another aspect of the present disclosure, the system may comprise a pump operated by an actuator and in communication with the control unit for conveying cooling fluid to the handset.

According to yet another aspect of the present disclosure, the driving system may comprise at least one power board connected to the control unit and apt to send to the handset a high-power signal suitable for generating ultrasounds.

According to yet another aspect of the present disclosure, the connection means may include circuit portions operationally connected to the power board and the control unit for transferring data and power to the handset.

According to yet another aspect of the present disclosure, the central unit may be configured to set the frequency range based on an operation mode.

The present disclosure also refers to an ultrasonic device comprising a driving system as illustrated above, a handset connected to this driving system and in operational communication therewith, and a tool connected to the handset.

In particular, the driving system and the handset may be configured to transmit ultrasounds to tools both for bone cement removal operations and for osteotomy operations, and the control unit may be configured to select from the memory unit an operation mode from among a plurality of stored operation modes, and to generate an error in the event that the response received from the handset does not correspond to the response expected for the type of tool associated therewith.

The control of the tool associated with the handset is performed by means of the aforementioned frequency scanning system which allows the type of tool to be identified and therefore an error to be generated in the event that the tool identified by means of scanning (namely by evaluating the impedance curve) does not correspond to the selected operation mode.

The present disclosure also refers to a method for driving an ultrasonic device for bone cement removal and/or osteotomy operations, comprising the steps of:

establishing at least a data connection between a control unit and a handset of the ultrasonic device;

sending a signal to the handset;

receiving from the handset a response to the signal sent; and checking an operating condition of the ultrasonic device based on this response.

According to an aspect of the present disclosure, the sending step may comprise sending to the handset said signal in the form of a signal having a frequency variable within a range of frequencies, and the checking step may comprise calculating at least one parameter indicative of the frequency response of the ultrasonic device, this checking step comprising a step of comparing the frequency response with stored data.

According to one aspect of the present disclosure, said calculated parameter may be the variation in impedance as a function of the signal frequency, providing an impedance curve representing the frequency response of the ultrasonic device.

Furthermore, the method may comprise a step of checking, by means of the central unit, whether the temperature inside the handset is higher than a threshold value.

According to one aspect of the present disclosure, the method may comprise a step of generating and optionally displaying an error signal in the case where the response received differs from an expected response. Furthermore, the step of displaying the error signal may also comprise displaying a solution for this error.

In particular, the method may comprise a step of selecting an operation mode from a plurality of stored operation modes, wherein said checking step (when the tool is associated with the handset) comprises checking whether a tool associated with the handset corresponds to the operation mode selected, and wherein the checking step comprises a comparison of different mathematical characteristics of the measured impedance curve with those of stored impedance curves.

In this way, the operator is able to recognize immediately whether the tool associated with the handset is not the correct one; this is particularly useful since the system according to the present disclosure allows the use of only a single handset for both bone cement removal operations and osteotomy operations.

According to yet another aspect of the present disclosure, the method may comprise a step of checking, based on the variation of the impedance curve, whether a tool associated with the handset is in contact with different materials.

Finally, the present disclosure refers to a computer program product for driving an ultrasonic device for bone cement removal and/or osteotomy operations, said computer program product comprising code portions adapted to control the system according to the method indicated above.

The features and advantages of the system and of the method according to the disclosure will become apparent from the following description of an embodiment thereof, given by way of non-limiting example with reference to the accompanying drawings.

DETAILED DESCRIPTION

Figure 1:
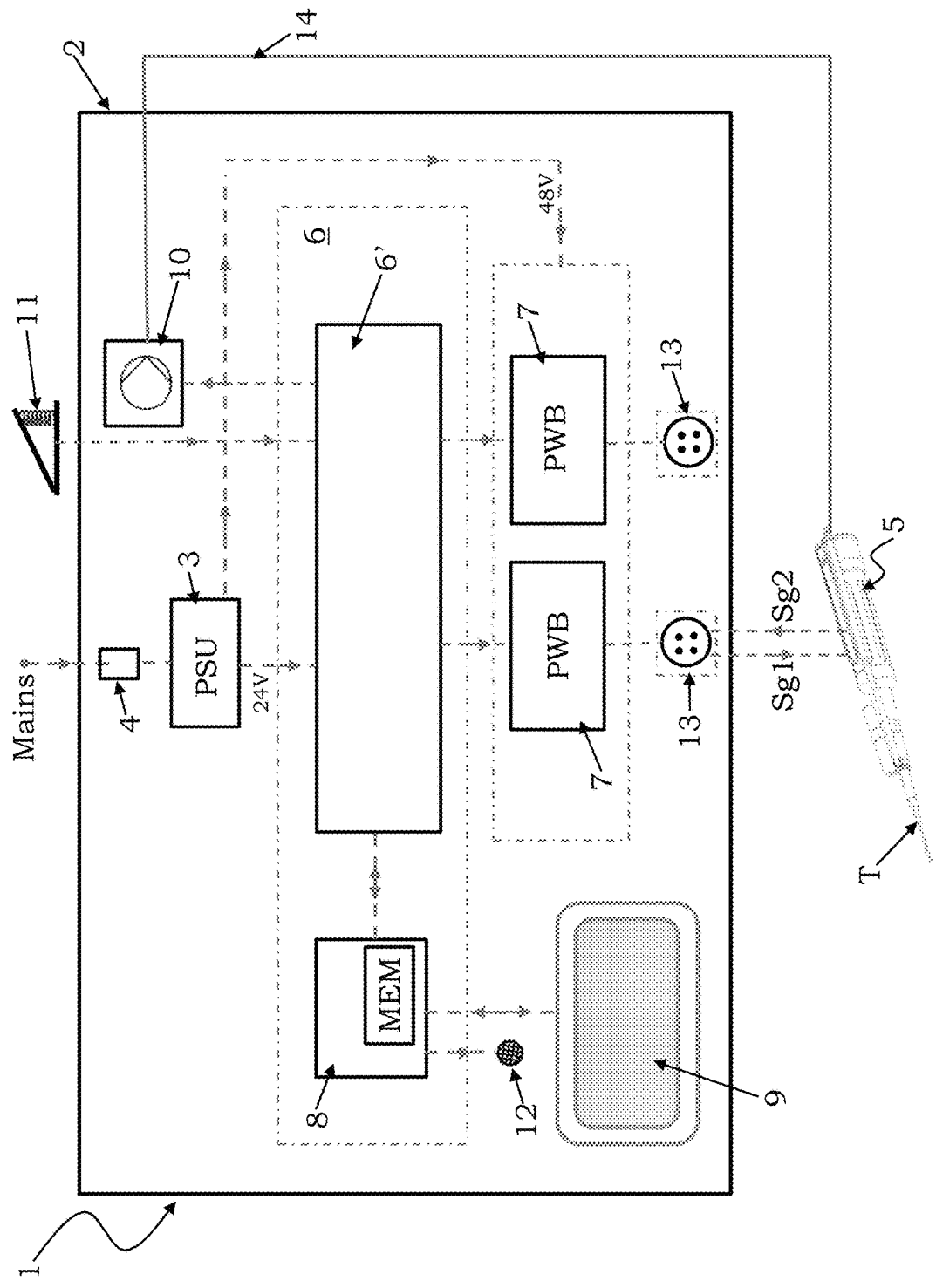
FIG. 1 shows a bock diagram of the driving system according to the present disclosure.

With reference to those figures, and in particular to the example of FIG. 1, a driving system for an ultrasonic device according to the present disclosure is globally and schematically indicated with the reference number 1.

It is worth noting that the figures represent schematic views and are not drawn to scale, but instead they are drawn so as to emphasize the important features of the disclosure. Moreover, in the figures, the different elements are depicted in a schematic manner, their shape varying depending on the application desired. It is also noted that in the figures the same reference numbers refer to elements that are identical in shape or function. Finally, particular features described in relation to an embodiment illustrated in a figure are also applicable to the other embodiments illustrated in the other figures.

The system 1 according to the present disclosure allows to drive, by implementing a given method, a handset which is able to generate ultrasounds for medical use. In particular, the system 1 is used for bone cement removal or also for osteotomy operations. It is also pointed out that, in the context of the present disclosure, the driving system 1 will also be indicated using the term "generator", as known in the art.

As shown schematically in FIG. 1, the system 1 comprises a housing 2 which encloses all its main components.

In particular, the system 1 comprises first of all a power supply unit 3 (indicated also as PSU) for converting the input voltage into a DC voltage to be supplied to the system components. The PSU 3 is therefore connected to the power supply input of the components of the system 1 to be powered, such as a control unit, a pair of power boards, etc. In order to reduce the electromagnetic interferences, an EMI filter 4 is arranged at the input of the PSU 3, as known in the art.

In an embodiment, the PSU 3 provides a DC voltage of 24 V, as well as a second DC voltage of 48 V which is used in particular for the generation of ultrasounds.

The driving system 1 according to the present disclosure is in fact intended to control the operation of a handset 5 used for the removal of bone cement during prosthesis revision procedures, as well as for cutting bone portions during osteotomy operations, by using ultrasounds. Conveniently, as it will be described in detail below, the system 1 allows only one type of handset 5 to be used for both the bone cement removal and osteotomy operations.

More specifically, the handset 5 comprises a main body which encloses and acts as a protective element for ultrasound generating means, which include a piezoelectric transducer and a horn, as known in the art. The handset 5 is connected to the driving system 1 by means of an electric cable, said electric cable being associated with the handset 5 by means of a suitable socket formed preferably at the distal end of the body of the handset 5. The piezoelectric transducer is designed to transform the electric energy supplied by the generator into mechanical vibrations, having a frequency of about 28.350 kHz. However, the system 1 according to the present disclosure is able to control the generation of ultrasounds within a wide range of frequencies, i.e. from 20 kHz to 100 kHz, with power levels ranging from 0 to 350 W, this system being particularly versatile and able to be used in various applications.

The horn of the handset 5 is apt to amplify and transfer the vibrations generated by the piezoelectric transducer to a tool T (also called "probe") connected to it.

The handset 5 therefore comprises connection means for connecting it to the tool T to which the generated ultrasounds are transmitted. Preferably, the connection means are in the form of a threaded connection at the proximal end of the horn.

The tools T associated with the handset 5 may have different forms and functions and will not be described in the present detailed description, the form and functions of these tools (as well as the internal structure of the handset 5) not forming part of the present disclosure. What is of importance for the purposes of the present description is that specific tools T are intended for specific operations, their form and size varying depending on the operations carried out and that, conveniently, the system 1 according to the present disclosure is able to drive a single handset 5 to be used in each operation and to identify the tool T associated with this handset, as will be described further below.

The system 1 according to the present disclosure comprises a central control unit 6 intended to control and manage its main functions, such as the generation of the ultrasounds, the communication between the various components of the system 1, the communication with the handset 5 and the control thereof.

In particular, the control unit 6 comprises a control board 6' which receives at its input 24 volts from the PSU 3 and is provided with its own integrated CPU which carries out specific instructions for controlling the ultrasounds.

For example, the CPU is configured to receive data from an analog-digital converter integrated in the control board 6' and connected to it, in particular in order to evaluate the actual frequency deviation of the generated ultrasounds from the nominal frequency, the amplitude of the output current and the output voltage and their temporal relationship. More particularly, the data input to the analog-digital converter is for example feedback data from the handset 5 or other components of the system. The CPU is therefore able to receive voltage and current data from the handset 5 in order to track the operating frequency thereof and therefore check the correct generation of the ultrasounds. In accordance with a method described further below, this CPU is structured and configured to check also the state of the piezoelectric transducer and the tools T associated with the handset 5. By way of a non-limiting example, the CPU of the control board 6' may be an ARM Cortex processor.

Furthermore the CPU of the control board 6' is operationally connected to a PWM controller (not shown in the figures), which is also integrated in the control board 6' and is adapted to manage phase-shifted PWM signals from which activation signals are generated, these activation signals being then used by a power board for the generation of ultrasounds, as will be described further below.

In an embodiment, the analog-digital converter and the PWM controller are integrated in the ARM Cortex processor and form part of the same control loop for management of the ultrasounds, said control loop being managed by the CPU as indicated above.

The control board 6' also comprises a power supply input apt to receive from the PSU 3 the DC voltage, in particular a 24 volt DC voltage. This power supply input is provided with mechanical elements which ensure protection against potential vibration of the control board 6'. Furthermore, the power supply input of the control board 6' also provides filtering of the high-frequency disturbance components so as to increase the performance of the system.

The control board 6' also comprises a portion for data communication with the handset 5 which allows the latter to be interfaced with the system 1. In particular, the control board 6' comprises a series of I/O ports for the communication with the handset 5. The communication with the handset 5 is managed by a communication buffer using the RS485 standard and, according to a preferred embodiment, it is performed by means of a communication circuit, as will be described below.

The system 1 according to the present disclosure also comprises means which produce as an output a high-voltage signal for the generation of the ultrasounds. In particular, the system 1 comprises at least one power board 7 connected to the control unit 6 and adapted to receive from it a series of signals (for example four PWM signals) and to generate, based on these signals, a signal with a power suitable for being sent to the handset 5 for generation of the ultrasounds.

The power board 7 receives the 24 volt and 48 volt power supplies from the PSU 3 and communicates with the control unit 6, as indicated above.

The power board 7 therefore comprises means able to generate and send to the piezoelectric transducer of the handset 5 a signal suitable for the generation of the ultrasounds.

Furthermore, the power board 7 is provided with its own CPU able to manage its operation independently and control the generation of the ultrasounds. For example, this CPU is adapted to generate a logic signal for driving those components of the power board 7 especially designed for the generation of the ultrasounds.

The CPU integrated in the power board 7 also receives data from the handset 5 for identification thereof and is able to manage a system for controlling the temperature of the power board 7 on the basis of data from a temperature sensor integrated therein.

Preferably, the system 1 comprises a pair of power boards 7 which are connected to two corresponding output channels, wherein during operation of the system 1 only one of these output channels is activated by the control unit 6. It is also pointed out that, although the system according to the present disclosure preferably has two power boards 7, any number of power boards may be provided depending on the requirements and/or the circumstances. The presence of a second additional power board 7 ensures a greater safety and efficiency of the system, since it provides a second output available during the operations.

Furthermore, the system 1 according to the present disclosure comprises connection means 13 which allow it to be connected to the handset 5, in particular allow connection between the handset 5 and the control unit 6, as well as the connection between the handset 5 and the power board 7. Each power board 7 is therefore preferably arranged between the control unit 6 and the connection means 13.

The connection means 13 are adapted to transmit to the handset 5 both data and the power supply necessary for the operation thereof and comprise a socket that allows physical interfacing of this handset 5 with the system 1.

The handset 5 is connected to the connection means 13 of the system 1 by means of a cable (not shown in the figures), which allows the transfer of both data and power supplies. This cable comprises a connector with four poles, two of which are used for the transmission of the signal for generating the ultrasounds (in particular two high-voltage signals, for example of 600 V), one of which is used for powering the handset and one for data transfer, this cable comprising an outer silicone sheath. Two screening braids are also provided for transfer of the reference potential, both of the earth protection and the communication bus.

The connection means 13 comprise a communication circuit (or communication interface) connected to the socket for connection to the handset 5. The communication circuit of the connection means 13 receives from the power board 7 the high-power signal for generating the ultrasounds and transmits it to the handset 5, and it is also connected to the control unit 6, in particular to the control board 6', in order to send/receive data and receive a 24 V power supply. The communication circuit is also provided with its own CPU which manages the data communication with the handset 5, said communication being performed using the RS485 standard.

In other words, the control unit 6 is able to communicate with the handset 5, for example in order to identify the handset itself, receive its activation signal or check the frequency of the ultrasounds, by means of the communication circuit of the connection means 13, which is provided with its own RS485 transceiver for continuous communication with said handset 5.

Similarly, the power board 7 sends to the handset 5 the high-voltage signal for generation of the ultrasounds by means of a special circuit of the communication means 13, said circuit being for example arranged alongside the communication circuit and being provided with means for isolation against nominal voltages of up to 600 V, so as not to interfere with the communication bus of the communication circuit, said screening being separate from the communication circuit of the handset.

The communication bus is instead used only for data communication, preferably by means of the RS485 transceiver, as indicated above.

The handset 5 has an architecture comprising a circuit similar to the communication circuit of the connection means 13 and in communication therewith. In particular, the handset 5 also is provided with a communication circuit (comprising for example a microprocessor) which in turn comprises a memory unit (for example an EEPROM memory) containing all the information useful for the identification thereof. For example, the memory unit of the handset 5 may comprise its serial number, which is communicated to the control unit 6 of the system 1 as soon as this handset 5 is connected, thus allowing immediate identification of the handset. The circuit also comprises a temperature sensor, means for driving an LED indicating the status of the system and, in a preferred embodiment, a Hall-effect sensor for activation thereof, the control unit 6 being configured to receive the data from these sensors.

The control unit 6 is therefore configured to communicate and receive data from this communication circuit integrated in the handset 5, said communication occurring via the communication circuit of the connection means 13, as indicated above. Essentially, the driving system 1 provides for the powering of the handset 5 (via the circuit of the connection means 13) and is characterized by a two-way (bidirectional) data exchange with said handset.

Furthermore, the control board 6' is operationally coupled to a memory unit MEM adapted to store data of the system 1. In particular, the memory unit MEM is included in the control unit 6 and is connected to control board 6' so as to keep stored all the operating parameters for the different types of operation, such as the operating parameters for the bone cement removal operations or the operating parameters for the osteotomy operations.

Even more particularly, the memory unit MEM is included in a computerized unit 8 of the control unit 6, this computerized unit 8 being in data and power communication with the control board 6' and supporting the software which manages all the functions and the logic of the system 1. The control board 6' is responsible for the management of the communication between the computerized unit 8 and the power board 7. In accordance with the architecture described above, the computerized unit 8 includes the system software, while the control board 6' includes the firmware. The control board 6' and the computerized unit 8 communicate with each other via the RS485 standard. Obviously, as illustrated above, the architecture described does not limit the scope of the present disclosure and other types of architecture may be used depending on the particular requirements and/or circumstances.

The memory unit MEM contains data matrices comprising all the information relating to the handset and the tools which can be associated with it, wherein all the operating parameters and the expected operating conditions are associated with each operation mode which can be selected. As will be described in detail below, the system 1 according to the present disclosure allows the operator to select the desired operation mode and automatically sets the parameters stored for that mode, whereby a given tool to be connected to the handset corresponds to said mode.

Advantageously according to the present disclosure, the control unit 6 is configured to send a signal Sg1 to the handset 5 and to receive from it a response Sg2 to said signal Sg1 which has been sent.

In particular, when executing the instructions of the software contained in the memory unit MEM, the control board 6' sends to the piezoelectric transducer of the handset 5 the signal Sg1, which may be defined as being a low-power stimulus signal, and measures the response Sg2 with the aim of checking an operating condition (or operating state) of the ultrasonic device based on said response Sg2 received from the handset 5.

Figure 2:
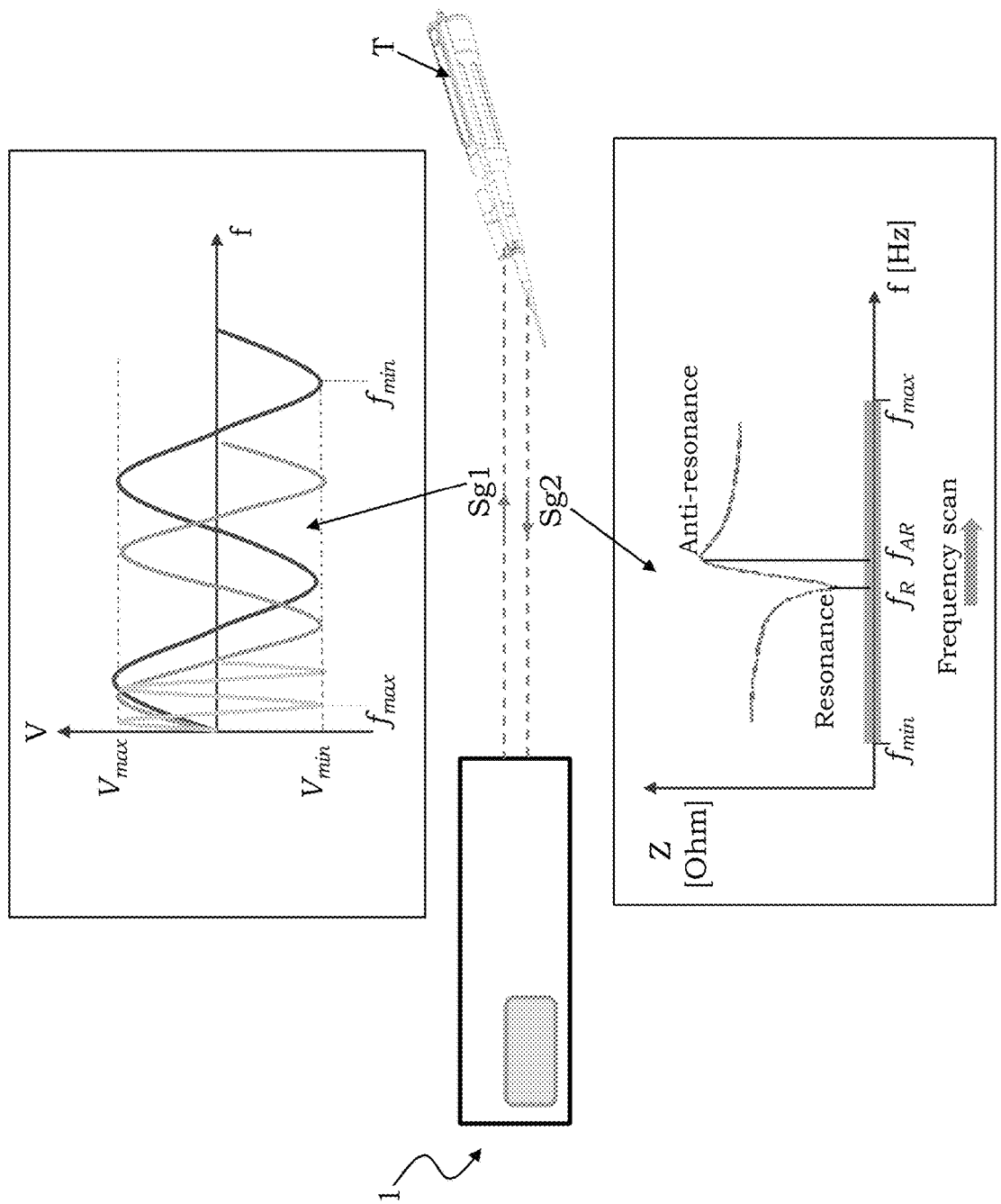
FIG. 2 schematically shows an exchange of signals between the driving system according to the present disclosure and a handset, for checking an operating condition.

The signal Sg1 which is sent to the handset 5 is in particular a signal with a frequency variable within a given frequency range, from a minimum frequency fmin to a maximum frequency fmax, as indicated in FIG. 2. Clearly the selected frequency range may vary depending on the application.

Even more particularly, the frequency range [fmin, fmax], which represents therefore the scanning range of the handset 5 and of any tool 5 associated with it, is chosen so that the expected resonance and anti-resonance frequencies of the tool T fall within this scanning range (which may be for example between 25 and 35 kHz). The resonance and anti-resonance frequencies are determined beforehand by means of numerical simulations of the response of the tool T to the variable-frequency signal Sg1. The signal Sg1 is therefore a wide-band and low-power stimulation signal (with frequency variable within the spectrum concerned), and therefore is not destructive even in the case of a fault of the handset or the cable. Moreover, the signal Sg1 is preferably a sinusoidal voltage signal, the amplitude of which is confined within a range defined between a minimum amplitude Vmin and a maximum amplitude Vmax, as shown in FIG. 2. It is also pointed out that, although the handset/tool system has a multitude of resonance frequencies, the scanning range is such that only one longitudinal resonance (and anti-resonance) frequency is identified.

Even more particularly, the system 1 of the present disclosure is such that, by means of the control unit 6 and the aforementioned signal Sg1, it is able to check a plurality of operating conditions of the ultrasonic system, including at least one of the following: the state of the piezoelectric transducer of the handset 5, the type of tool T associated with the handset 5, and/or the state of said tool T. In the context of the present disclosure, the particular operation mode is for the example the type of operation to be performed, while "operating condition" is understood as meaning for example the state of the handset or the type of tool associated with it, said operating condition being checked by means of the signal Sg1 and the response Sg2 and compared with the expected values for the particular operation mode selected. This is particularly interesting since, in accordance with the present disclosure, a single handset 5 is used for all the types of operations and therefore an optimum feedback is obtained for the operator.

The signal Sg1 sent to the handset 5 is the same both for evaluating the state of the piezoelectric transducer (namely for evaluating the response of the handset 5 without the tool T connected) and for evaluating the handset 5 with the tool T connected thereto, also checking the quality of the connection.

During the frequency scanning, the driving system 1 is configured to measure continuously the electric current absorbed and the electric potential based on the response Sg2. In an embodiment, knowing the temporal variations of the voltage V and the current I, V(t) and I(t), respectively, the driving system 1 is configured to calculate, by means of the central unit 6, the impedance (in a manner known in the art) as a function of the time of the system, Z(t). In this way, knowing the frequency variation of the signal as a function of the time, f(t), it is possible to create a graph [f(t), Z(t)] which represents the so-called impedance curve of the system. In other words, by means of the response signal Sg2, it is possible to calculate the impedance curve of the system, namely the impedance as a function of the scanning frequency, as shown in FIG. 2, thus providing the frequency response of the system.

For example, when a system comprising the handset 5 and tool T is scanned, as shown in FIG. 2, owing to the longitudinal resonances and anti-resonances (namely the longitudinal deformations which propagate in the mechanical system), the impedance curve shows two characteristic peaks: the first peak identifies the resonance frequency fr (minimum value thereof) while the second peak identifies the anti-resonance frequency fAR (maximum value thereof). In addition to the aforementioned values, it is possible to obtain characterizing information also from the specific behaviour of the first and second derivatives Z'(f) and Z"(f). Each handset-tool system has its own characteristic impedance curve, such that different tools, owing to their form factor (generally they are narrow and elongated), modify substantially the impedance curve and therefore are characterized by their own specific curve, such that the type or category of tools connected to the handset 5 may be identified automatically by means of an analysis of the said impedance curve, as will be illustrated below.

The analysis of the impedance curve also allows the state of the piezoelectric system to be determined and in particular any breakages in the mechanical components of the handset-tool system to be detected.

The handset 5 alone, instead, does not have such a characteristic impedance curve.

In the case where the operating condition checked by the control unit 6 is the state of the piezoelectric transducer of the handset 5 (and therefore when the tool T is not associated with the handset), the signal Sg1 is defined as above and the response Sg2 of the handset 5 to this signal Sg1 which is sent corresponds to the frequency response curve of the piezoelectric transducer, namely corresponds to the characteristic response (again in the form of an impedance curve) of the handset alone assessed without the tool T, providing an indication of the state of this transducer. The frequency response curve of the piezoelectric transducer, measured when no tools T are associated with the handset 5, therefore represents the basic model of the ultrasound generating system which comprises the piezoelectric transducer and the whole mechanical amplification and transmission system. It has its peak at the emission frequency of a piezoelectric transducer which is functioning correctly (e.g. about 28.350 kHz).

In the context of the present disclosure, the term "frequency response" therefore always indicates the variation in impedance of the system which is stressed by a variable-frequency voltage. Obviously, other physical parameters equivalent to the impedance may be calculated following the stimulus, if required by the circumstances.

The memory unit MEM comprises data relating to the optimum frequency response curve of the piezoelectric transducer, so that it is possible to check the state of this transducer by carrying out a comparison between the measured real curve and the stored expected curve, as will be described further below in greater detail.

As illustrated above, in the case where a tool T is associated with the handset 5 (and therefore in the case where the control unit 6 checks the type of tool T associated with the handset 5 or the state of this tool), the response of the handset 5 to the sent signal Sg1 varies depending on the type of tool T connected, since the different form of the tools leads to different responses, in particular different resonances.

In particular, the control unit 6, in response to the sending of the check signal Sg1 (which is the same as that for the handset 5 alone), is configured to measure the characteristic impedance curve of the tool T upon variation of the frequency within the frequency range as previously defined, said impedance curve being unique for each tool T or in general for each category of tools T.

The driving system 1 is therefore configured to recognize the tool T by performing a comparison with the stored data, comparing in particular the resonance frequencies.

In this case, the memory unit MEM comprises data relating to the impedance curve as a function of the frequency for all the tools T which may be associated with the handset 5, and the control unit 6 is configured to compare the measured response curve with the stored expected response curve for a given tool associated with the operation mode selected by the operator.

In general, the comparison carried out by the control unit 6 allows the settings of the ultrasonic system to be checked for their correctness, and an error signal is generated in the case the values measured do not tally with the expected values, thereby increasing the efficiency, the reliability and the safety of the system.

Even more particularly, the evaluation of the response signal Sg2 of the system is carried out over the whole scanning range, defining a data vector (and therefore a multi-dimensional vector having modulus and phase for each frequency of the band) having a frequency step variable between 0.1 Hz and 20 Hz. The aforementioned evaluation is based on the calculation of the distances between the expected vector and the vector defined according to the response Sg2 (and therefore not only on the mono-dimensional values of the resonance frequencies).

In other words, preferably, the checking of the tool associated with the handset is performed not only by comparing the resonance frequency value with an expected value for that tool, but also by comparing (by means of classification and clustering) the whole impedance curve of the tool T with a set (or "cluster") of stored reference curves of similar tools. The control unit 6 is therefore configured to implement a multi-dimensional comparison which takes into account different mathematical characteristics of the impedance curves (form, maximum values, minimum values, first derivative, second derivative, etc.). Clearly, the aforementioned comparison also involves, at least indirectly, a comparison between the resonance and anti-resonance frequencies. Consequently, the algorithms implemented by the control unit allow to compare the entire impedance curve in its mathematical characterization (values of the resonance and anti-resonance frequencies, first, second and third derivatives, etc.), in particular by means of machine learning or artificial intelligence techniques, with reference models (sets of previously classified impedance curves) which characterize the expected behaviour that is specific for each handset-tool combination.

An error is generated by the control unit 6 if the measured values do not match with the expected values which have been stored.

The driving system 1 is configured to provide the response signal Sg2 by means of the feedback from the voltage and current vectors which power the handset 5, suitably conditioned and galvanically isolated from the output of the driving system 1, which by means of two galvanic barriers, both for the voltage feedback and for the current feedback, electrically separate the signals sent to the analog-digital converter from the signals sent to the piezoelectric transducer. The isolation barrier uses the transmission of the magnetic field to separate the high-voltage primary circuits from the secondary measurement circuits and is such that it does not alter the phase relationship between the respective voltage and current vectors generated. The voltage and current feedback of the secondary circuits of the barrier is conditioned by wide-band, linear, differential amplifiers before being applied to the analog circuits for extraction of the effective value and the power factor of the original parameters and then applied to the analog sampling circuits of the analog-digital converter.

As mentioned above, according to the present disclosure, the system 1 allows the operator to select the desired operation mode from a plurality of operation modes stored in the memory unit MEM, each operation mode corresponding to a specific tool T to be associated with the handset 5.

In this connection, the system 1 according to the present disclosure comprises a user interface 9 configured to allow the entry and display of operating parameters or the selection of the desired operation mode from among a plurality of operation modes whose operating parameters have been stored beforehand in the memory unit MEM, said user interface 9 thus allowing direct interaction with the system. Based on the settings entered by the operator via the user interface 9, the control unit 6 sets the most appropriate inputs/outputs for the power board 7.

Preferably, the user interface 9 is a touch screen interface, even though other solutions obviously fall within the scope of the present disclosure.

Figure 3:
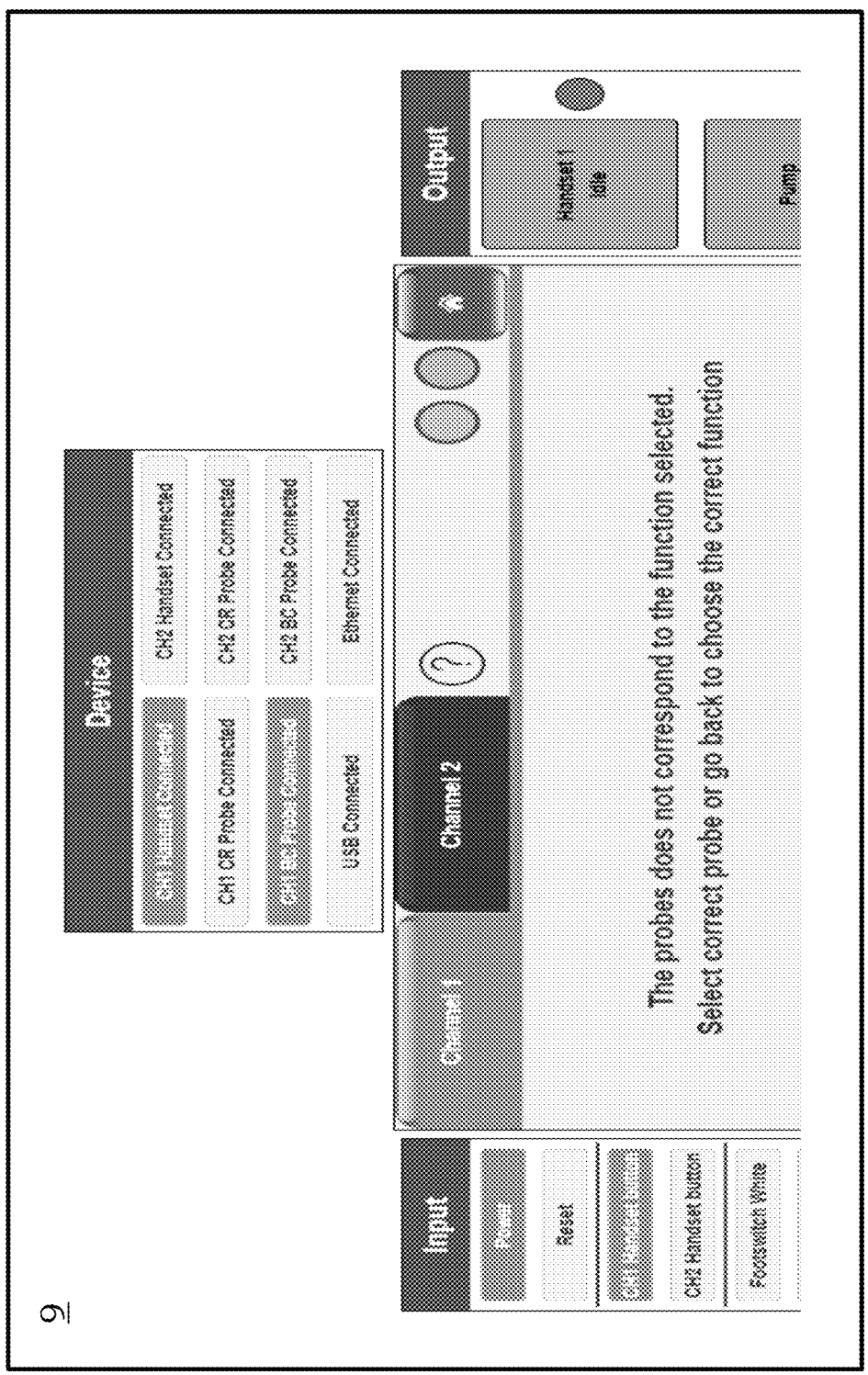
FIG. 3 shows an example of a user interface of the driving system according to the present disclosure.

The operation of the user interface 9 is controlled by the computerized unit 8 and FIG. 3 shows an example of such an interface in accordance with an embodiment of the present disclosure.

In particular, the user interface 9 is such as to display to the operator initially a plurality of operation modes to be selected and, once the desired mode has been selected, the corresponding operating parameters are automatically set. At this point, the operator has the option of activating (for example by pressing a given pushbutton) the function for checking the state of the handset 5 and/or the tool T associated with it (namely the operating condition check), wherein the control unit 6 is configured to generate the control signal Sg1 and compare the response Sg2 received with information stored in the memory unit MEM, as indicated above. In accordance with an embodiment of the present disclosure, the checking of the state of the system may also be performed automatically each time the system is activated. In this way, the check may be performed either manually or automatically or following a confirmation request of the user interface 9, for example after a tool T has been associated with the handset 5.

As shown in FIG. 3, in the case where the measured response differs from the expected response, an error signal is generated by the central unit 6 and is converted into an error message which is displayed by means of the user interface 9.

With reference again to FIG. 1, acoustic signaling means 12 (such as a loudspeaker) are also provided, said means 12 being able to signal to the operator any error or danger situations.

Furthermore, it is pointed out that, when a tool T is associated with the handset 5, the response Sg2 of the handset 5 to the input signal Sg1 is determined by the combination of the effect due to the piezoelectric transducer and the effect due to the presence of the tool T, and consequently any deterioration of the piezoelectric transducer causes a deviation of the characteristic response of the tools from that which is expected.

Advantageously, the control unit 6 is also configured to discriminate between the response due to the piezoelectric transducer and the response due to the type of tool T used.

The control unit 6 is in fact able to implement an automatic learning procedure which makes use of machine learning and/or artificial intelligence techniques. In particular, the learning procedure is based on classification and clustering. In this way, by means of the machine learning procedure, the control unit 6 is able to process the response Sg2 from the handset 5 so as to determine the extent to which the response is due to the deterioration of the piezoelectric transducer. This is particularly advantageous since a variation of the response of the piezoelectric transducer (for example due to aging) could result in incorrect identification of the tool T associated with the handset 5.

In this way, conveniently, it is possible to establish in an efficient and reliable manner whether the tools T mounted on the handset 5 effectively correspond to the operation mode selected.

The control unit 6 is also able to check, by means of an analysis of the frequency response of the handset 5, the state of the tools T, for example the presence of any fissures which cause a variation in the response.

Furthermore, it is known that, during operation of the ultrasonic system, the temperature of the tool T associated with the handset 5, as well as the temperature of the treated area, may reach high levels which are potentially dangerous for the instrument and the patient. For this reason, the handset 5 comprises a duct for circulation of a cooling medium which is supplied at the tool and therefore at the treated zone of the patient.

The flow of the cooling medium (which normally consists of a physiological solution) is ensured by means of a peristaltic volumetric pump 10 which is incorporated in the housing 2 of the driving system 1 and is able to control and meter the flowrate of the cooling medium.

The pump 10 is operated by an actuator 11, such as a footswitch, this actuator 11 being connected to the central unit 6, in particular to the control board 6' and sending an activation signal to said control board 6'. The control board 6', in response to the activation signal received from the actuator 11, sends in turn an activation signal to the pump 10 which is thus able to convey the cooling fluid to the handset 5 via a duct 14 connected to the duct of the handset 5. The operation of the pump 10 is therefore controlled by the control board 6', with which it is able to communicate.

By means of a series of pipes passing through the pump 10, it is possible to connect a cooling medium container (which may be situated outside the housing 2 of the system 1) to the duct 14 of the system 1 and the handset 5, the latter being able to convey the correct amount of cooling medium into the treatment zone.

Again with the aim of reducing the problems associated with the increase in temperature of the treated area, the control unit 6 is configured to time the operation of the handset 5. More specifically, at predefined intervals (for example every 30 seconds) the activation of the piezoelectric transducer is interrupted for a given time period (generally a few seconds), with the interruption of the power supply towards the ultrasound system. This mode of operation ensures indirect control of the temperature and also gives the operator time to clean and check the working area. Furthermore, such a functional feature is able to overcome the problems associated with drilling of the cortical bone.

In any case, as illustrated above, the handset 5 is provided internally with a temperature sensor and the control unit 6 is able to receive data relating to the temperature reached inside the handset 5. In the case of risk of damage to the device, the control unit 6 is able to interrupt for a given period of time (for example a few seconds) the power supply and therefore the generation of the high-power signal emitted by the power board 7.

Furthermore, the control unit 6, which is in communication with the handset 5, is able to signal any excessive pressure and/or flexing of the tool exerted by the surgeon during the operations. This feedback ensures optimum use of the instrument, at the same time safeguarding the piezoelectric transducer and the tools T, thus increasing the safety for the operator and the patient.

Furthermore, the system 1 according to the present disclosure is able to alert the operator (for example by means of a message displayed on the user interface 9 or an acoustic signal emitted by the acoustic signaling means 12) when the tool T comes into contact with materials having different density, such as steel, titanium, etc. For this purpose, the control unit 6 is configured to implement feedback control, for example based on the measurement of the frequency of the ultrasonic resonances, which may vary depending on the material with which the tool T makes contact.

As mentioned above, conveniently according to the present disclosure, the driving system 1 is such that a same handset 5 may be used both for bone cement removal and for osteotomy operations; in this case it is only required to select and associate with the handset 5 the tool T suitable for the operation to be performed. The system 1 according to the present disclosure is therefore able to drive a same piezoelectric transducer for different types of operation, providing different powers and managing different frequencies so as to be compatible with both applications. The adjustment of the power of the piezoelectric transducer is managed by the control unit 6, ensuring extreme flexibility of the system.

The possibility of checking the correctness of the tool T associated with the handset 5 by means of frequency scanning, as described above, is thus particularly advantageous, since both tools for bone cement removal and tools for performing osteotomy operations may be associated with a same handset.

Figure 4:
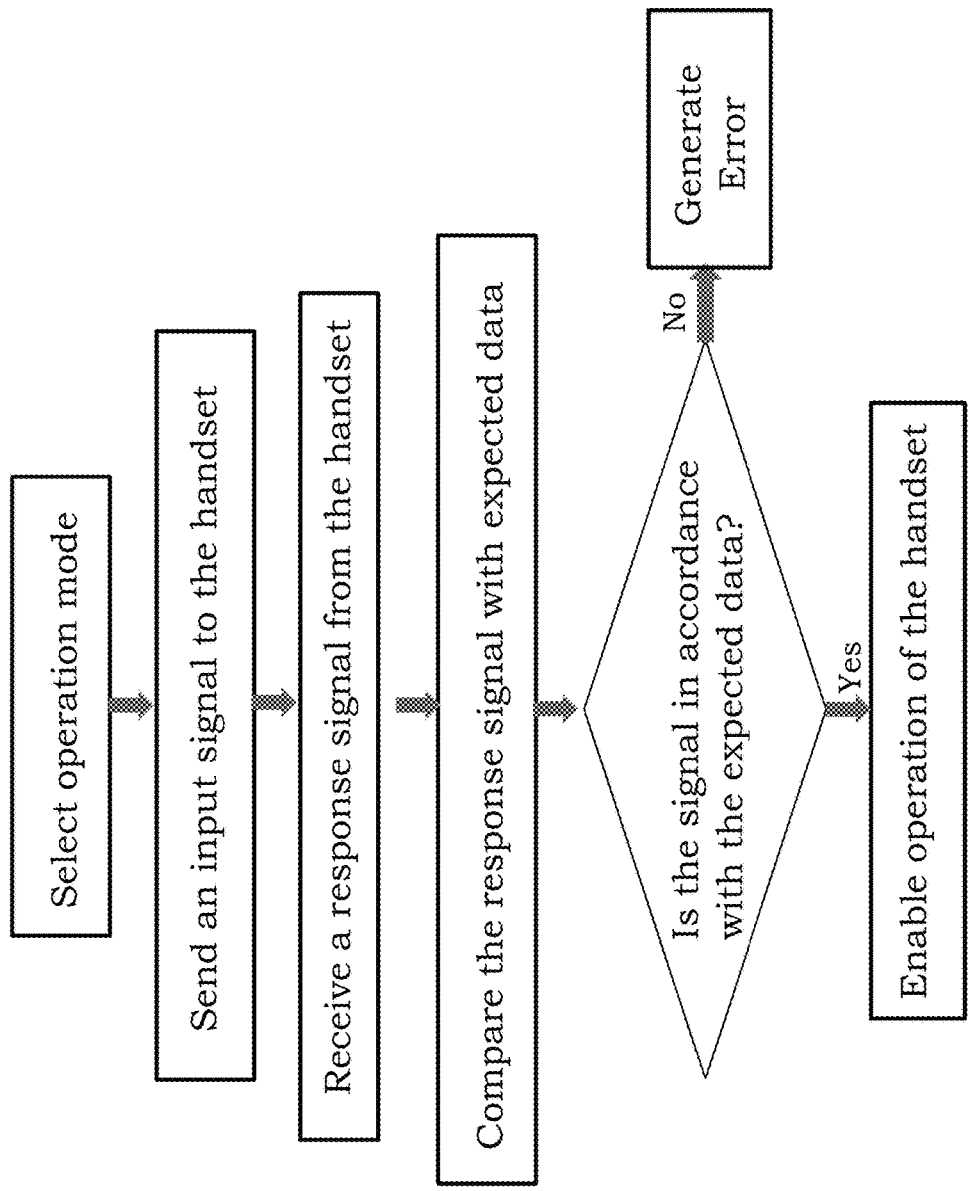
FIG. 4 shows a flow diagram illustrating a method according to the present disclosure.

With reference now to FIG. 4, the present disclosure also refers to a method for driving an ultrasonic device for bone cement removal and/or osteotomy operations, said method comprising the preliminary step of establishing a connection between a control unit 6 and a handset 5 of the ultrasonic device by means of specially designed connection means 13.

The method then comprises a step of sending a signal Sg1 to the handset 5 and a subsequent step of receiving from the handset 5 a response Sg2 to said sent signal Sg1.

Finally, advantageously, based on the response received from the handset 5, a step of checking an operating condition of the ultrasonic device is performed.

In particular, in accordance with the method according to the present disclosure, the checking step comprises a step of sending to the handset 5 a variable-frequency test signal as defined above, said step being followed by a step of comparing the frequency response curve of the piezoelectric transducer with previously stored information. In this way, when no tools are associated with the handset 5, it is possible to check the state of the piezoelectric transducer and therefore the condition of said handset 5.

Conveniently, the method also comprises a step of selecting, via a suitable user interface 9, an operation mode from among a plurality of stored operation modes. For example, it is possible to choose between a bone cement removal mode and an osteotomy operation mode. Once the desired mode has been selected, all the operating parameters are automatically set, and the operator is able to carry out the operation. Clearly, it will be necessary to associate with the handset 5 the appropriate tool T for the mode selected, said handset 5 comprising a single threaded connection for each type of tool and therefore being able to be used both for cement removal operations and for osteotomy operations.

Even more conveniently, the method comprises a step for checking that a tool T, or a category of tools, associated with the handset 5 corresponds to the operation mode selected.

More specifically, the check comprises firstly a step of sending to the handset 5 the signal Sg1 defined above and then measuring the characteristic impedance curve of the tool T upon variation of the frequency in response to the signal sent.

Furthermore, the method comprises a step of generating and displaying an error signal if the response from the handset 5 differs from the expected response.

In particular, a step of generating and displaying an error signal is envisaged if the responses measured are different from the previously stored expected responses. In particular a comparison at least of the measured resonance frequencies and the expected frequencies is carried out (generally a comparison of data vectors is carried out, as described above) and the error signal is generated if the frequencies measured are outside a predefined range around the expected frequencies.

Furthermore, the aforementioned step of displaying the error signal also comprises the indication of a solution to said error, so as to assist the operator in the most efficient manner possible. Help messages for the operator are in fact provided both during set-up and during error resolution, significantly improving the interaction between system and operator.

If instead no errors are generated, the operation of the handset 5 is enabled, said handset 5 being therefore ready to generate the ultrasounds for example following the pressing of a given control button by the operator.

A temperature control step is also provided: in particular it is possible to check whether the temperature inside the handset 5 is above a given threshold value.

Furthermore, a step of checking whether a tool T associated with the handset 5 comes into contact with various materials is also provided, this being based in particular on the measurement of the variation in the ultrasonic resonance frequencies.

In conclusion, the present disclosure provides to equip an ultrasonic device with a driving/control system configured to send to a handset of the device an input signal and to measure the characteristic response of the handset and/or the tool associated with the handset to this input signal, this response being compared with expected responses previously stored in the memory of the driving system. In this way, the present disclosure allows data exchange between the handset and the driving system, providing the operator with useful information such as feedback about the state of the handset and the type of tools associated with it and/or their state.

Advantageously according to the present disclosure, the proposed system is configured to exchange data bidirectionally with the handset and, following suitable checks, provides the operator with a plurality of feedbacks, increasing the efficiency and at the same time the safety of the ultrasonic device.

In fact, once the operation to be performed has been selected, the operator is firstly guided when choosing the tool suitable for the operation selected, and the system, by executing the instructions of a suitable computer program, allows to evaluate whether the chosen tool corresponds to the selected mode, and at the same time evaluate the state of the piezoelectric transducer, thus carrying out a full diagnosis of the ultrasonic system. This diagnosis is carried out in real time and very rapidly, by executing a frequency scan of the handset by means of the control unit of the system according to the present disclosure.

The proposed system therefore effectively solves the technical problem of the present disclosure, improving significantly the interaction between ultrasonic system and operator, providing immediate feedback about the operating conditions of said ultrasonic system.

There is also the possibility of using a single handset for each type of operation, the system according to the present disclosure allowing a feedback relating to the type of tool used, and therefore being able to indicate whether the tool associated with the handset is the right one.

Finally, it is also envisaged the possibility of measuring the state of the tools, again with the aim of improving the performance and the safety of the ultrasonic device.

From the foregoing it will be appreciated that, although specific embodiments of the disclosure have been described herein for purposes of illustration, various modifications may be made without deviating from the spirit and scope of the disclosure, all included in the protection scope as defined by the appended claims.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for driving an ultrasonic device for bone cement removal and/or osteotomy operations, comprising:
    a control unit;
    a memory unit; and
    connection means for connecting together the control unit and a handset of the ultrasonic device, wherein the control unit is configured to:
        send a signal to the handset;
        receive from the handset a response to said sent signal; and
        check an operating condition of the ultrasonic device based on said response;
    wherein said sent signal is a signal with a frequency variable within a frequency range, and wherein, based on said response, the control unit is configured to calculate at least one parameter indicative of a frequency response of the ultrasonic device,
    wherein the calculated parameter is a variation in impedance as a function of the frequency, providing an impedance curve representing the frequency response of the ultrasonic device, and
    wherein, in said check of the operating condition, the control unit is configured to perform an analysis of the whole measured impedance curve, said analysis being based on reference models.

2. The system according to claim 1, wherein the operating condition of the ultrasonic device checked by the control unit comprises at least one of a state of a piezoelectric transducer of the handset, a type of a tool associated with the handset, and/or a state of the tool.

3. The system according to claim 1, wherein the control unit is configured to measure the impedance of a tool associated with the handset or, when the tool is not associated with the handset, the impedance of a piezoelectric transducer of the handset upon variation of the frequency, and wherein the memory unit comprises data relating to the frequency response expected for the tool associated with the handset and/or data relating to the frequency response expected for the piezoelectric transducer of the handset, the control unit being further configured to compare the impedance curve with expected values stored in the memory unit.

4. The system according to claim 1, wherein the control unit is configured to compare different mathematical characteristics of the impedance curve, including maximum values, minimum values, first derivative and second derivative, with those of known impedance curves which have been previously stored.

5. The system according to claim 1, wherein the control unit is configured to:
    select from the memory unit an operation mode from among a plurality of stored operation modes; and
    generate an error when the response received from the handset does not correspond to stored data associated with the selected operation mode.

6. The system according to claim 1, wherein the control unit is adapted to implement an automatic learning procedure which adopts machine learning and/or artificial intelligence techniques.

7. The system according to claim 1, comprising a user interface configured to allow at least one of: an input of operating parameters, a display of operating parameters, or a selection of an operation mode from a plurality of operation modes whose operating parameters have been previously stored in the memory unit.

8. The system according to claim 1, wherein the control unit is configured to communicate with and to receive data from an electronic unit incorporated in the handset.

9. The system according to claim 8, wherein said data comprises at least a serial number of the handset.

10. The system according to claim 1, wherein the control unit comprises a control board and a computerized unit which includes the memory unit, in data communication with each other.

11. The system according to claim 1, comprising a pump operated by an actuator and in communication with the control unit for conveying cooling fluid to the handset.

12. The system according to claim 1, comprising at least one power board connected to the control unit and adapted to send to the handset a high-power signal suitable for generating ultrasound.

13. The system according to claim 12, wherein the connection means include circuit portions operatively connected to the at least one power board and the control unit for transferring data and power to the handset.

14. The system according to claim 1, wherein the control unit is configured to set the frequency range based on an operation mode.

15. An ultrasonic device comprising:
    a driving system for driving an ultrasonic device for bone cement removal and/or osteotomy operations, the driving system in turn including:
        a control unit;
        a memory unit; and
        connection means for connecting together the control unit and a handset of the ultrasonic device,
    wherein the control unit of the driving system is configured to:
        send a signal to the handset;
        receive from the handset a response to said sent signal; and
        check an operating condition of the ultrasonic device based on said response,
    wherein said sent signal is a signal with a frequency variable within a frequency range, and wherein, based on said response, the control unit is configured to calculate at least one parameter indicative of a frequency response of the ultrasonic device, wherein the calculated parameter is a variation in impedance as a function of the frequency, providing an impedance curve representing the frequency response of the ultrasonic device, and wherein, in said check of the operating condition, the control unit is configured to perform an analysis of the whole measured impedance curve, said analysis being based on reference models, the ultrasonic device further comprising:
- a handset connected to the driving system and in operational communication therewith; and
- a tool connected to the handset.

16. The ultrasonic device according to claim 15, wherein the driving system and the handset are configured to transmit ultrasounds to tools both for bone cement removal operations and for osteotomy operations, and wherein the control unit is configured to:
- select from a memory unit an operation mode from a plurality of stored operation modes; and
- generate an error when the response received from the handset does not correspond to the response expected for the tool associated therewith.

17. A method for driving an ultrasonic device for bone cement removal and/or osteotomy operations, comprising the steps of:
- establishing at least a data connection between a control unit and a handset of the ultrasonic device;
- sending a signal to the handset;
- receiving from the handset a response to the sent signal; and
- checking an operating condition of the ultrasonic device based on said response;

wherein the signal has a frequency variable within a frequency range, wherein the method further comprises, based on said response, calculating at least one parameter indicative of a frequency response of the ultrasonic device, wherein the calculated parameter is a variation in impedance as a function of the frequency, providing an impedance curve representing the frequency response of the ultrasonic device, and wherein said checking the operating condition comprises performing an analysis of the whole measured impedance curve, said analysis being based on reference models.

18. The method according to claim 17, comprising a step of generating an error signal when the frequency response differs from an expected stored response.

19. The method according to claim 18, wherein the step of generating the error signal also comprises displaying a solution for the error.

20. The method according to claim 17, comprising a step of selecting an operation mode from a plurality of stored operation modes, wherein checking the operating condition comprises checking whether a tool associated with the handset corresponds to the selected operation mode and comparing different mathematical characteristics of the impedance curve with those of stored impedance curves.

21. The method according to claim 17, further comprising a step of checking, by the control unit, whether a temperature inside the handset is higher than a threshold value.

* * * * *